United States Patent [19]

Barlozzari et al.

[11] Patent Number: 5,741,892

[45] Date of Patent: Apr. 21, 1998

[54] PENTAPEPTIDES AS ANTITUMOR AGENTS

[75] Inventors: Teresa Barlozzari, Wellesley; Andreas Haupt, Westborough; Bernd Janssen, Marlborough, all of Mass.; Christian Griesinger, Oberursel, Germany; Daniel Belik, Frankfurt, Germany; Michael Boretzky, Offenbach, Germany; George R. Pettit, Paradise Valley, Ariz.

[73] Assignee: Basf Aktiengesellschaft, Rheinland-Pfalz, Germany

[21] Appl. No.: 688,334

[22] Filed: Jul. 30, 1996

[51] Int. Cl.$^6$ .................................................. C07K 7/00
[52] U.S. Cl. .................................. 530/330; 514/17
[58] Field of Search ............................ 530/330; 514/17

[56] References Cited

U.S. PATENT DOCUMENTS

| | | | |
|---|---|---|---|
| 4,816,444 | 3/1989 | Pettit et al. | 514/17 |
| 5,502,032 | 3/1996 | Haupt et al. | 514/17 |
| 5,504,191 | 4/1996 | Pettit et al. | 530/330 |
| 5,530,097 | 6/1996 | Pettit et al. | 530/330 |

FOREIGN PATENT DOCUMENTS

| | | |
|---|---|---|
| 0 398 558 | 11/1990 | European Pat. Off. . |
| 0 598 129 | 5/1994 | European Pat. Off. . |
| 93/23424 | 11/1993 | WIPO . |

OTHER PUBLICATIONS

Pettit, G. R., et al., "Antineoplastic Agents 337. Synthesis of Dolastatin–10 Structural Modifications," Anti–Cancer Drug Design, 10: 529–544 (1995).

Miyazaki, K., et al., "Synthesis and Antitumor Activity of Novel Dolastatin–10 Analogs," Chem. Pharm. Bull., 43(10): 1706–1718 (1995).

Pettit, G.R. et al., "Isolation of Dolastatins 10–15 From the Marine Mollusc Dolabella Auricularia," Tetrahedron, 49(41):9151–9170 (1993).

Pettit, G.R., et al., "The Dolastatins 20. A Convenient Synthetic Route to Dolastatin 15," Tetrahedron, 50(42):12097–12108 (1994).

Pettit, G.R., et al., "The Isolation and Structure of a Remarkable Marine Animal Antineoplastic Constituent: Dolastatin 10", J. Am. Chem. Soc. 109: 6883–6885 (1987).

Bai, R., et al., "Structure–Activity Studies with Chiral Isomers and with Segments of the Antimitotic Marine Peptide Dolastatin 10", Biochemical Pharmacology 40(8): 1859–1864 (1990).

Pettit, G. R, et al., "Antineoplastic Agents. 220. Synthesis of Natural (−)-Dolastatin 15", J. Am. Chem. Soc., 113: 6692–6693 (1991).

Pettit, G. R., et al., "Isolation and Structure of the Cytostatic Linear Depsipeptide Dolastatin 15", J. Org. Chem., 54: 6005–6006 (1989).

Bai, R., et al., "Dolastatin 15, a potent antimitotic depsipeptide derived from Dolabella auricularia. Interaction with tubulin and effects on cellular microtubules", 1–Pharmacology Abstract 117: 103735g p. 41 (1992).

Pettit, G. R., et al., "Isolation and Structure of the Cytostatic Depsipeptide Dolastatin 13 from the Sea Hare Dolabella auricularia", J. Am. Chem. Soc., 111(13): 5015–5017 (1989).

Primary Examiner—Cecilia J. Tsang
Assistant Examiner—C. Delacroix-Muirheid
Attorney, Agent, or Firm—Hamilton, Brook, Smith & Reynolds, P.C.

[57] ABSTRACT

The present invention provides anti-tumor peptides of Formula I,

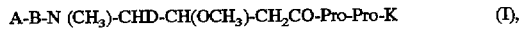

A-B-N(CH$_3$)-CHD-CH(OCH$_3$)-CH$_2$CO-Pro-Pro-K  (I), and the acid salts thereof. A is an amino acid residue of the formula (CH$_3$)$_2$N—CHX—CO, wherein X is a normal or branched alkyl group. B is an amino acid residue selected from the group consisting of valyl, isoleucyl, leucyl, and 2-t-butylglycyl. D is a normal or branched C$_3$–C$_4$-alkyl group. K is a t-butoxy group or a substituted amino group.

An additional embodiment of the present invention is a method for treating a malignancy in a mammal, such as a human, comprising administering to the mammal an effective amount of a compound or compounds of Formula I in a pharmaceutically acceptable composition.

8 Claims, No Drawings

PENTAPEPTIDES AS ANTITUMOR AGENTS

BACKGROUND OF THE INVENTION

A series of short peptides with significant activity as cell growth inhibitors have been isolated from the Indian Ocean sea hare *Dolabella auricularia* (Pettit et al., *J. Am. Chem. Soc.* 109: 6883–6885 (1987); Beckwith et al., *J. Natl. Cancer Inst.* 85, 483–88 (1993); U.S. Pat. No. 4,816,444; European Patent Application Publication No. 398558). These peptides are referred to as Dolastatins 1–15. Of these, Dolastatins 10 and 15 are the most potent cell growth inhibitors. Dolastatin 15, for example, inhibits the growth of the National Cancer Institute's P388 lymphocytic leukemia (PS system) cell line, a strong predictor of efficacy against various types of human malignancies. Dolastatin 10 and Dolastatin 15 effectively inhibit tubulin polymerization and growth of four different human lymphoma cell lines (Bai et al., *Biochem. Pharmacol.* 39: 1941–1949 (1990); Beckwith et al., supra (1993)).

The minute amounts of the Dolastatin peptides present in *Dolabella auricularia* (about 1 mg each per 100 kg sea hare) and the consequent difficulties in purifying amounts sufficient for evaluation and use, have motivated efforts toward the synthesis of the more promising of these compounds, including Dolastatin 10 (Pettit et al., *J. Am. Chem Soc.* 111: 5463–5465 (1989); Roux et al. *Tetrahedron* 50: 5345–5360 (1994); Shiori et al. *Tetrahedron* 49: 1913–1924 (1993)). Synthetic Dolastatin 10, however, suffers from disadvantages which include poor solubility in aqueous systems and the need for expensive starting materials for its synthesis. These disadvantages, in turn, have led to the synthesis and evaluation of structurally modified Dolastatin 10 derivatives (European Patent Application, Publication No. WO 93/03054; Japanese Patent Application No. 06234790; U.S. patent application Ser. No. 08/178,529).

A need persists for synthetic compounds with the biological activity of Dolastatin 10 which have useful aqueous solubility and can be produced efficiently and economically.

SUMMARY OF THE INVENTION

The present invention provides peptides which have antitumor or anti-neoplastic activity. These compounds are of Formula I,

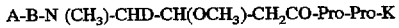

A-B-N(CH$_3$)-CHD-CH(OCH$_3$)-CH$_2$CO-Pro-Pro-K     (I), and include the acid salts thereof. In Formula I:

A is an amino acid residue of the formula (CH$_3$)$_2$N—CHX—CO, wherein X is a normal or branched C$_{3-4}$-alkyl group.

B is an amino acid residue selected from the group consisting of valyl, isoleucyl, leucyl, and 2-t-butylglycyl.

D is a normal or branched C$_3$–C$_4$-alkyl group.

K is a t-butoxy group or a substituted amino group.

Another aspect of the present invention includes pharmaceutical compositions comprising a compound of Formula I and a pharmaceutically acceptable carrier.

An additional embodiment of the present invention is a method for treating a malignancy in a mammal, such as a human, comprising administering to the mammal an effective amount of a compound or compounds of Formula I in a pharmaceutically acceptable composition.

DETAILED DESCRIPTION OF THE INVENTION

The present invention relates to peptides having antitumor or antineoplastic activity. It also includes pharmaceutical compositions comprising these compounds and methods for treating cancer in a mammal, including a human, by administration of these compositions to the mammal.

Applicants have discovered that structural modification of Dolastatin 10 results in novel compounds with a surprisingly improved therapeutic potential for the treatment of neoplastic diseases, as compared to Dolastatin 10. Furthermore, the compounds of the present invention can be conveniently synthesized, as described below in detail.

Compounds of the present invention include antitumor peptides of Formula I:

A-B-N(CH$_3$)-CHD-CH(OCH$_3$)-CH$_2$CO-Pro-Pro-K     (I), wherein

A is an amino acid residue of the formula (CH$_3$)$_2$N—CHX—CO, wherein X is a normal or branched C$_{3-4}$-alkyl group;

B is an amino acid residue selected from the group consisting of valyl, isoleucyl, leucyl, and 2-t-butylglycyl;

D is a normal or branched C$_{3-4}$-alkyl group; and

K is a t-butoxy group or a substituted amino group. Examples of suitable amino groups include: —N(C$_{1-3}$-alkyl) C$_{1-3}$-alkyl, normal or branched —NH—C$_{1-8}$-alkyl, —NH—C(CH$_3$)$_2$CN, —NH—C(CH$_3$)$_2$CCH, —NH—C(CH$_3$)$_2$CH$_2$CH$_2$OH, —NH'C (CH$_3$)$_2$CH$_2$OH, —NH—C$_{3-8}$-cycloalkyl, —NH—[3,3,0]-bicyclooctyl, —NHCH (CH$_3$)CH(OH)C$_6$H$_5$, —NH-quinolyl, —NH-pyrazyl, —NH—CH$_2$-benzimidazolyl, —NH-adamantyl, —NH—CH$_2$-adamantyl, —NH—CH (CH$_3$) -phenyl, —NH—C (CH$_3$)$_2$-phenyl, —N(C$_{1-4}$-alkoxy)-C$_{1-4}$-alkyl, —N (C$_{1-4}$-alkoxy)—CH$_2$-phenyl, —N(C$_{1-4}$-alkoxy) phenyl, —N (CH$_3$)O-phenyl, —NH—(CH$_2$)$_v$-phenyl (v=0,1,2, or 3), —NH—(CH$_2$)$_m$-naphthyl (m=0 or 1), —NH—(CH$_2$)$_w$-benzhydryl (w=0,1, or 2), —NH-biphenyl, —NH-pyridyl, —NH—CH$_2$-pyridyl, —NH—CH$_2$-CH$_2$-pyridyl, —NH-benzothiazolyl, —NH-benzoisothiazolyl, —NH-benzopyrazolyl, —NH-benzoxazolyl, —NH-(CH$_2$)$_m$-fluorenyl (m=0 or 1), —NH-pyrimidyl, —NH—(CH$_2$)$_m$-indanyl (m=0 or 1), —NH—(CH$_2$CH$_2$O)$_y$—CH$_2$CH$_3$ (y=0,1,2,3,4, or 5), —NH—(CH$_2$CH$_2$O)$_y$—CH$_3$ (y=0,1,2,3,4, or 5), —NH—NH—C$_6$H$_5$, —NH—N(CH$_3$)C$_6$H$_5$, —NH—NH—CH$_2$—C$_6$H$_5$, and —NH—N(CH$_3$)CH$_2$—C$_6$H$_5$.

K can also be selected from among the following:

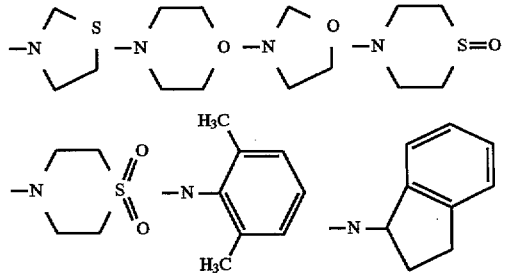

-continued
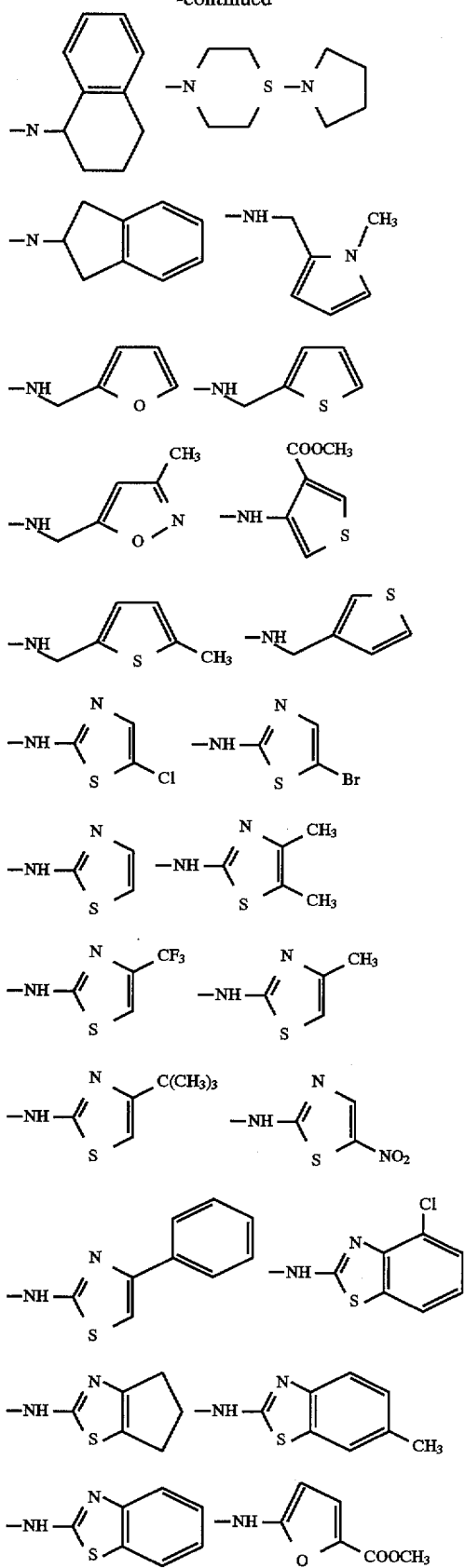
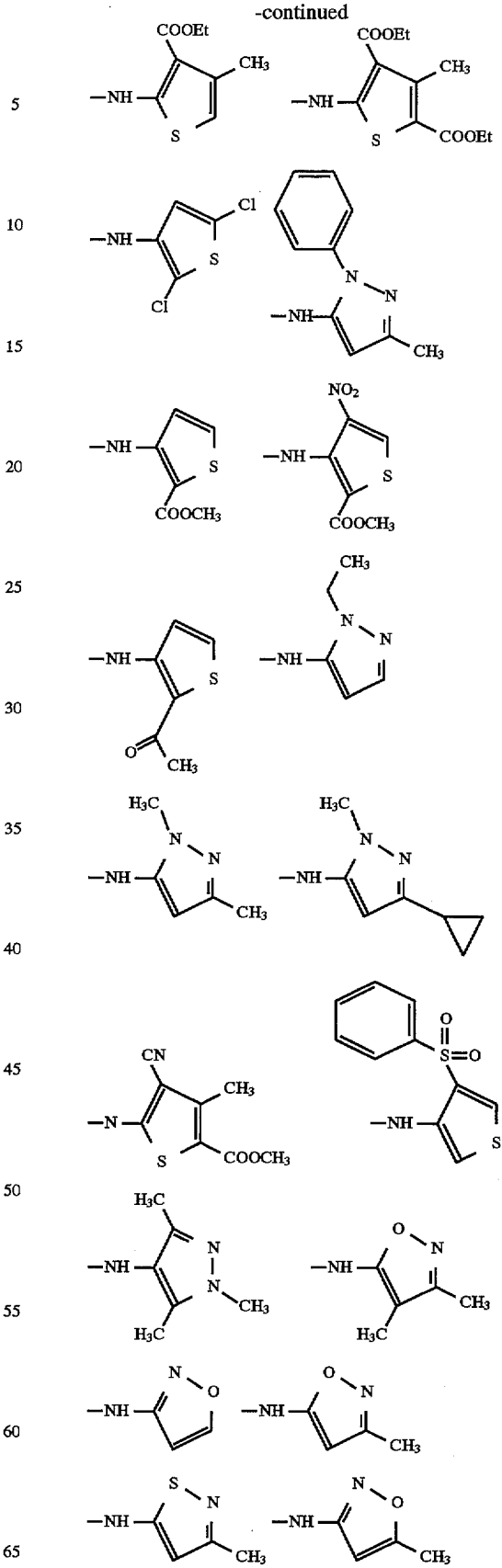

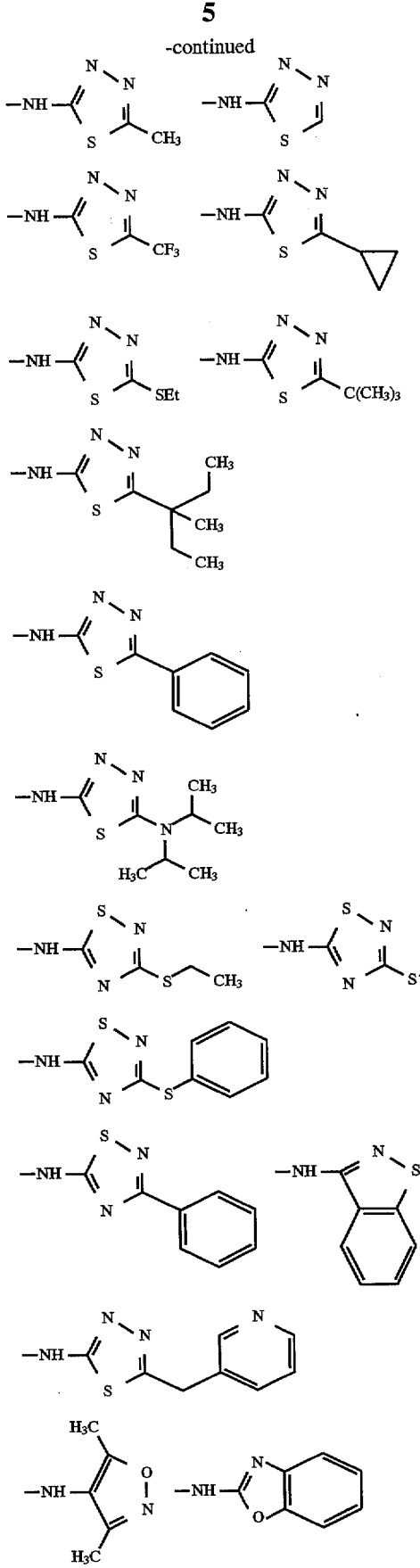

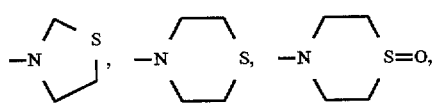

Preferred compounds of the present invention are of Formula I in which:

A is an amino acid residue of the formula $(CH_3)_2N$—CHX—CO, wherein X is an isopropyl, t-butyl or sec-butyl group;

B is an amino acid residue selected from the group consisting of valyl, isoleucyl and 2-t-butylglycyl;

D is an isopropyl, t-butyl or sec-butyl group;

K is a t-butoxy group or a substituted amino group selected from among the following: —$NHCH_3$, —$NHCH_2CH_3$, —$NH(CH_2)_2CH_3$, —$NH(CH_2)_3CH_3$, —$NH(CH_2)_4CH_3$, —$NH(CH_2)_5CH_3$, —$NHCH(CH_3)_2$, —$NHCH(CH_2CH_3)_2$, —$NHCH(CH_2CH_2CH_3)_2$, —$NHC(CH_3)_2$, —$NHCH[CH(CH_3)_2]_2$, —$NHCH(CH_2CH_3)CH_2CH_2CH_3$, —$NHCH(CH_3)CH_2CH_3$, —$NHCH_2CH_2F$, —$NHC(CH_3)_2CH_2CH_3$, —$NHCH(CH_3)CH(CH_3)_2$, —$NHCH(CH_3)C(CH_3)_3$, —$NHCH(CH_3)CH_2CH_2CH_3$, —$NHCH_2CH(CH_3)_2$, —$NHCH_2C(CH_3)_3$, —NH-cyclopropyl, —NH-cyclobutyl, —NH-cyclopentyl, —NH-cyclohexyl, —NH-cycloheptyl, —$N(CH_3)$ $OCH_3$, —$N(CH_3)_2$, —$N(CH_3)OCH_2CH_3$, —$N(CH_3)OCH_2CH_2CH_3$, —$N(CH_3)OCH(CH_3)_2$, —$N(CH_2CH_3)OCH_3$, —$N(CH_2CH_3)OCH_2CH_3$, —$N(CH_3)OCH_2C_6H_5$, —$N(OCH_3)CH_2$—$C_6H_5$, —$N(CH_3)OC_6H_5$, —NH—$CH_2$—$C_6H_5$, —$NH(CH_2)_2C_6H_5$, —$NH(CH_2)_3C_6H_5$, —$NHCH(CH_3)CH(OH)C_6H_5$, —NH—$CH_2$-cyclohexyl, —NH-indanyl-(1), —NH—$CH_2CF_3$, —$NHCH(CH_2F)_2$, —$NHC(CH_3)_2CH_2OH$, —$NH(CH_2CH_2O)_2CH_2CH_3$, —$NHC(CH_3)_2CN$, —NH-quinolyl, —NH-pyrazyl, —NH-adamantyl (2), —NH-adamantyl(1), —NH—$CH_2$-naphthyl, —NH-benzhydryl, —NH-biphenyl, —NH-pyridyl, —NH—$CH_2$-pyridyl, —NH—$CH_2$—$CH_2$-pyridyl, —NH-benzothiazolyl, —NH-benzoisothiazolyl, —NH-benzopyrazolyl, —NH-benzoxazolyl, —NH-fluorenyl, —NH-pyrimidyl, —NH—$CH_2$-(4-methyl)thiazolyl(2), —NH—$CH_2$-furanyl(2), —NH—$CH_2$-thienyl(2), —NH—$CH_2$-(5-methyl)thienyl(2), —NH-thiazolyl(2), —NH-isoxazolyl(3), —NH-(3-methyl)isoxazolyl(5), —NH-(3-methyl)isothiazolyl(5), —NH-(5-trifluoromethyl)thiadiazolyl(2), —NH-(5-cyclopropyl)thiadiazolyl(2), —NH-(4,5-dimethyl)thiazolyl(2), —NH-(5-methyl)thiadiazolyl(2), or K is selected from among the heterocyclic amino groups shown below.

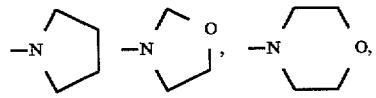

Synthetic Methods

The compounds of the present invention can be prepared by known methods of peptide synthesis. Thus, the peptides can be assembled sequentially from individual amino acids or by linking suitable small peptide fragments. In sequential assembly, the peptide chain is extended stepwise, starting at the C-terminus, by one amino acid per step. In fragment coupling, fragments of different lengths can be linked together, and the fragments in turn can be obtained by sequential assembly from amino acids or by fragment coupling of still shorter peptides.

In both sequential assembly and fragment coupling, it is necessary to link the units by forming an amide linkage, which can be accomplished via a variety of enzymatic and chemical methods. Chemical methods for forming the amide linkage are described in detail in standard references on peptide chemistry, including Müller, *Methoden der organischen Chemie* Vol. XV/2, 1–364, Thieme Verlag, Stuttgart, (1974); Stewart and Young, *Solid Phase Peptide Synthesis*, 31–34 and 71–82, Pierce Chemical Company, Rockford, Ill. (1984); Bodanszky et al., Peptide Synthesis, 85–128, John Wiley & Sons, New York, (1976). Preferred methods include the azide method, the symmetric and mixed anhydride method, the use of in situ generated or preformed active esters, the use of urethane protected N-carboxy anhydrides of amino acids and the formation of the amide linkage using coupling reagents, such as carboxylic acid activators, especially dicyclohexylcarbodiimide (DCC), diisopropylcarbodiimide (DIC), 1-ethoxycarbonyl-2-ethoxy-1,2-dihydroquinoline (EEDQ), 1-ethyl-3-(3-dimethylaminopropyl)carbodiimide hydrochloride (EDCI), n-propane-phosphonic anhydride (PPA), N,N-bis (2-oxo-oxazolidinyl)imido-phosphoryl chloride (BOP-Cl), bromo-tris-pyrrolidinophosphonium hexafluorophosphate (PyBrop), diphenylphosphoryl azide (DPPA), Castro's reagent (BOP, PyBop), O-benzotriazolyl-N,N,N', N'-tetramethyluronium salts (HBTU), O-azabenzotriazolyl-N,N,N',N'-tetramethyluronium salts (HATU), diethylphosphoryl cyanide (DEPCN), 2,5-diphenyl-2,3-dihydro-3-oxo-4-hydroxythiophene dioxide (Steglich's reagent; HOTDO), and 1,1'-carbonyldiimidazole (CDI). The coupling reagents can be employed alone or in combination with additives such as N,N-dimethyl-4-aminopyridine (DMAP), N-hydroxybenzotriazole (HOBt), N-hydroxybenzotriazine (HOOBt), N-hydroxyazabenzotriazole (HOAt), N-hydroxysuccinimide (HOSu) or 2-hydroxypyridine.

Although the use of protecting groups is generally not necessary in enzymatic peptide synthesis, reversible protection of reactive groups not involved in formation of the amide linkage is necessary for both reactants in chemical synthesis. Three conventional protective group techniques are preferred for chemical peptide synthesis: the benzyloxycarbonyl (Z), the t-butoxycarbonyl (Boc) and the 9-fluorenylmethoxycarbonyl (Fmoc) techniques. Identified in each case is the protective group on the α-amino group of the chain-extending unit. A detailed review of amino-acid protective groups is given by Müller, *Methoden der organischen Chemie* Vol. XV/1, pp 20–906, Thieme Verlag, Stuttgart (1974). The units employed for assembling the peptide chain can be reacted in solution, in suspension or by a method similar to that described by Merrifield, *J. Amer. Chem. Soc.* 85 2149 (1963). Particularly preferred methods are those in which peptides are assembled sequentially or by fragment coupling using the Z, Boc or Fmoc protective group technique.

Solvents suitable for peptide synthesis include any solvent which is inert under the reaction conditions, especially water, N,N-dimethylformamide (DMF), dimethyl sulfoxide (DMSO), acetonitrile, dichloromethane (DCM), 1,4-dioxane, tetrahydrofuran (THF), N-methyl-2-pyrrolidone (NMP), ethyl acetate and mixtures of these solvents.

For coupling of the amino acid following the the N-methylated γ-amino acid derivative, the use of either BOC-protected amino acid N-carboxy anhydrides (NCAs), Z-protected NCAs or the use of pivaloyl chloride or HATU as the condensing agent is most advantageous for this type of coupling.

Peptides which are dialkylated at the amino terminus can be prepared using the appropriate N,N-dialkylamino acid as a building block or by hydrogenating N-unsubstituted peptides in solution in the presence of an appropriate aldehyde or ketone and a catalyst such as palladium on charcoal.

The various non-naturally occurring amino acids disclosed herein can be obtained from commercial sources or synthesized from commercially available materials using methods known in the art. For example, the moiety —$NR^3$—CHD—CH($OCH_3$)$CH_2$CO— can be prepared according to published procedures (Shiori et al. in *Peptide Chemistry*, Yanaihara, ed. (1989); Pettit et al., *J. Am. Chem. Soc.* 111: 5463 (1989); Shiori et al., *Tet. Lett.* 931–934 (1991); Koga et al., *Tet. Lett.* 2395–2398 (1991)).

Methods of Use of the Claimed Compounds

In another embodiment, the present invention comprises a method for partially or totally inhibiting formation of, or otherwise treating (e.g., reversing or inhibiting the further development of) solid tumors (e.g., tumors of the lung, breast, colon, prostate, bladder, rectum, or endometrial tumors) or hematological malignancies (e.g., leukemias, lymphomas) in a mammal, for example, a human, by administering to the mammal a therapeutically effective amount of a compound or a combination of compounds of Formula I. The compound(s) of Formula I can be administered alone or in conjunction with other drugs, such as other anti-cancer drugs or in a pharmaceutical composition further comprising an acceptable carrier or diluent, and, optionally, other drugs. Administration can be by any means which are appropriate for pharmaceutical, preferably oncological, agents, including oral and parenteral means such as subcutaneously, intravenously, intramuscularly and intraperitoneally, nasally or rectally.

The dosage to be administered to the mammal, such as a human, is a therapeutically effective amount of a compound described herein. The therapeutically effective amount can be administered in a single dose or multiple doses in a given period of time (e.g., a single daily dose or two or more doses a day). As used herein, "therapeutically effective amount" is an amount sufficient to inhibit (partially or totally) formation of a tumor or a hematological malignancy or to reverse development of a solid tumor or other malignancy or prevent or reduce its further progression. For a particular condition or method of treatment, the dosage is determined empirically, using known methods, and will depend upon factors such as the biological activity of the particular compound employed; the means of administration; the age, health and body weight of the recipient; the nature and extent of the symptoms; the frequency of treatment; the administration of other therapies; and the effect desired. A typical daily dose will be from about 0.5 to about 50 milligrams per kilogram of body weight by oral administration and from about 0.05 to about 20 milligrams per kilogram of body weight by parenteral administration.

The compounds of the present invention can be administered in conventional solid or liquid pharmaceutical administration forms, for example, uncoated or (film-) coated tablets, capsules, powders, granules, suppositories or solutions. These are produced in a conventional manner. The active substances can, for this purpose, be processed with conventional pharmaceutical aids such as tablet binders, fillers, preservatives, tablet disintegrants, flow regulators, plasticizers, wetting agents, dispersants, emulsifiers, solvents, sustained release compositions, antioxidants and/ or propellant gases (cf. H. Sücker et al.: Pharmazeutische Technologie, Thieme-Verlag, Stuttgart, 1978). The administration forms obtained in this way typically contain from about 1 to about 90% by weight of the active substance.

The following examples are intended to illustrate the invention but are not to be considered limitations of the invention.

EXAMPLES

The naturally-occurring amino acids are abbreviated in the examples using the known three-letter code. Other abbreviations employed are: TFA=trifluoroacetic acid; Ac =acetic acid; DCM=dichloromethane; DMSO= dimethylsulfoxide; Bu=butyl; Et=ethyl; Me=methyl; Bzl =benzyl; LDA=lithium diisopropylamide; LHMDS=lithium hexamethyldisilazide; HMPA=hexamethylphosphoric triamide.

General Materials and Methods

The compounds of the present invention are synthesized by classical solution synthesis using standard Z- and Boc-methodology as discussed above.

Purification was carried out by crystallization from the appropriate solvents or mixtures thereof, by medium pressure chromatography (stationary phase: HD-SIL C-8, 20–45 micron, 100 Angstrom; mobile phase: gradient with A=0.1% TFA/water, B=0.1% TFA/MeOH), or by preparative HPLC (stationary phase: Waters Delta-Pak C-18, 15 micron, 100 Angstrom; mobile phase: gradient with A=0.1% TFA/water, B=0.1% TFA/MeOH or 0.1% TFA/Acetonitril). The purity of the resulting products was determined by analytical HPLC (stationary phase: 100 2.1 mm VYDAC C-18, 300 Angstrom; mobile phase: acetonitrile-water gradient, buffered with 0.1% TFA, 40% C). Characterization was by mass spectroscopy (ESI or FAB-MS).

Example 1

Synthesis of (3R,4S)-4-[N-(N,N-dimethyl-L-valyl-L-Valyl)-N-methylamino)-3-methoxy-5-methyl-hexanoyl-prolyl-prolyl-thiazolyl(2)-amide (compound 1; SEQ ID NO:1)

Synthesis of t-Butyl-(4S)-4-(N-benzyloxycarbonylamino)-5-methyl-3-oxohexanoate

To an ice-cooled solution of Z-Valine (5 g, 19.9 mmol) in 60 ml tetrahydrofuran was added N,N'-carbonyldiimidazole (3.55 g, 22.3 mmol) in one portion and the resulting mixture stirred for 3 h. t-Butyl acetate (13.5 ml, 100 mmol) was added dropwise to a solution of LDA (90 mmol in tetrahydrofuran (270 ml) at −78° C. After 30 min, the imidazolide solution was added dropwise via double-ended needle to the enolate. The resulting mixture was stirred for 2 h until the temperature rose to −15° C. The reaction was quenched with 400 ml saturated aqueous NH$_4$Cl and extracted with ether (3×200 ml). The combined organic extracts were washed with 2N aqueous HCl (50 ml), saturated aqueous NaHCO$_3$ (2×50 ml), dried over magnesium sulfate and evaporated to dryness in vacuo. The residue was purified by column chromatography on silica gel using ethyl acetate-hexane (1:4) as an eluent to give the product as a colorless oil (6.88 g).

MS: calc. monoisotopic mass 349.19; found ESI-: 348.1

Synthesis of t-butyl-(3R,4S)-4-(N-benzyloxycarbonylamino)-3-hydroxy-5-methyl-hexanoate To a solution of t-butyl-(4S)-4-(N-benzyloxycarbonylamino)-5-methyl-3-oxohexanoate (6.0 g, 17.1 mmol) in 70 ml ethanol at 0° C. was added potassium borohydride (3.23 g, 58.8 mmol). After stirring for 4 h at 0° C. and 12 h at room temperature, the reaction mixture was acidified with glacial acetic acid to pH 4 and concentrated in vacuo. The residue was dissolved in a mixture of 200 ml ethyl acetate and 200 ml water. After additional washings of the aqueous phase with ethyl acetate (3×50 ml), the combined organic extracts were dried over magnesium sulfate and concentrated in vacuo. The crude product was purified by column chromatography on silica gel using ethyl acetate-hexane (1:4) as eluent to give the alcohol as a white solid (5.31 g).

MS: calc. monoisotopic mass: 351.2; found ESI+: 352.2

Synthesis of t-butyl-(3R,4S)-4-(N-benzyloxycarbonyl-N-methylamino)-3-methoxy-5-methyl-hexanoate A solution of t-butyl-(3R,4S)-4-(N-benzyloxycarbonylamino)-3-hydroxy-5-methyl-hexanoate (3.027 g, 8.624 mmol) in tetrahydrofuran (40 ml) was added to a solution of LHMDS (24.0 mmol) in HMPA (4.5 ml, 25.7 mmol) and tetrahydrofuran (40 ml) at −78° C. After stirring for 20 min, methyltriflate (5.68 ml, 51.7 mmol) was added. After 1 h, the reaction was stopped by adding 70 ml aqueous 10% citric acid. The mixture was extracted with ethyl acetate (3×). The combined organic extracts were washed with saturated aqueous NaHCO$_3$ (100 ml), dried over magnesium sulfate and concentrated in vacuo. The crude product was purified by column chromatography on silica gel, using ethyl acetate-hexane (1:4) as eluant to give the desired product as a colorless oil (2.456 g).

MS: calc. monoisotop. mass 379.24; found FAB-MS [M+H]$^+$: 380

Synthesis of t-butyl-(3R,4S)-4-(N-methylamino)-3-methoxy-5-methylhexanoate

To a solution of t-butyl-(3R,4S)-4-(N-benzyloxycarbonyl-N-methylamino)-3-methoxy-5-methylhexanoate (3.855 g, 10.17 mmol) in 100 ml methanol was added 10% Pd/C (0.541 g) and the mixture was hydrogenated until completion of the deprotection (tlc control). The catalyst was removed by filtration and the filtrate concentrated in vacuo. The resulting amorphous solid (2.49 g) can be crystallized from ether by adding a solution of HCl in dioxane.

MS: calc. monoisotopic mass 245.2; found FAB-MS [M+H]$^+$246

Synthesis of t-butyl-(3R,4S)-4-[N (benzyloxycarbonyl-L-valyl)N-methylamino]-3-methoxy-5-methylhexanoate To a solution of Z-valine (3.672 g, 14.6 mmol) and pivaloyl chloride (1.8 ml, 14.6 mmol) was added diisopropylethylamine (2.5 ml 14.6 mmol) at −15° C. After 1 h, t-butyl-(3R,4S)-4-(N-methylamino)-3-methoxy-5-methylhexanoate (1.79 g, 7.3 mmol) and diisopropylethylamine (1.25 ml, 7.3 mmol) were added. The resulting mixture was stirred for 3 h at 0° C., 20 h at room temperature and then concentrated in vacuo. The residue was dissolved in ethyl acetate (100 ml), washed with 10% aqueous citric acid (2×30 ml) and saturated aqueous NaHCO$_3$ (30 ml), dried over magnesium sulfate and concentrated in vacuo. The crude product was purified by column chromatography on silica gel using ethyl acetate-hexane (1:4) as eluant to give the dipeptide as a colorless oil (1.804 g).

MS: calc. monoisotopic mass 478.3; found FAB-MS [M+H]$^+$479

Synthesis of t-butyl-(3R,4S)-4-[N (L-valyl)-N-methylamino)-3-methoxy-5-methylhexanoate To a solution of t-butyl-(3R,4S)-4-[N-(benzyloxycarbonyl-L-valyl)-N-methylamino)-3-methoxy-5-methylhexanoate (1.804 g, 3.77 mmol) in methanol (60 ml) was added 10% Pd/C (0.26 g) and the mixture was hydrogenated until completion (tlc control). The catalyst was removed by filtration and the filtrate was concentrated in vacuo to give the deprotected dipeptide unit (1.27 g).

MS: calc. monoisotopic mass 344.27; found FAB-MS [M+H]$^+$345

Synthesis of t-butyl-(3R,4S)-4-[N(N,N-dimethyl-L-valyl-L-valyl)-N-methylamino)-3-methoxy-5-methyl-hexanoate t-Butyl-(3R,4S)-4-[N-(L-valyl)-N-methylamino)-3-methoxy-5-methylhexanoate (0.357 g, 1.038 mmol) and N,N-dimethylvaline (0.301 g, 2.076 mmol) were dissolved in 3 ml DMF and cooled to 0° C. DEPC (0.496 ml, 2.283 mmol) was added, followed by diisopropylethylamine (0.391 ml, 2.283 mmol). After stirring at 0° C. for 3 h and at room temperature for 16 h, the reaction mixture was diluted with saturated aqueous NaHCO$_3$ (20 ml) and washed with toluene/ethylacetate 2:1 (3×). The combined organic layers were extracted with 2N HCl (3×10 ml). The aqueous phase was then neutralized with NaHCO$_3$ and extracted with toluene/ethyl acetate (2:1) (3×20 ml). The organic layer was dried over magnesium sulfate and concentrated in vacuo. The crude product was purified by crystallization from ether by adding a solution of HCl in dioxane to give the tripeptide as a white solid (0.433 g).

MS: calc. monoisotopic mass 471.37; found FAB-MS [M+H]$^+$472

Synthesis of (3R,4S)-4-[N-(N,N-dimethyl-L-valyl-L-valyl)-N-methylamino]-3-methoxy-5-methylhexanoic acid To a solution of t-butyl-(3R,4S)-4-[N-(N,N-dimethyl-L-valyl-L-valyl)-N-methylamino]-3-methoxy-5-methylhexanoate (0.22 g, 0.433 mmol) in dichloromethane (2 ml) was added trifluoroacetic acid (2 ml). After stirring for 2 h, the reaction mixture was concentrated in vacuo. Reevaporation of the residue with toluene (5×10 ml) gave the deprotected product (0.268 g) which was used for the next step without further purification.

MS: calc. monoisotopic mass 415.3; found FAB-MS [M+H]$^+$416

Synthesis of N-(t-butyloxycarbonyl)-prolylprolyl-thiazolyl(2)amide

Boc-prolyl-proline (1 g, 3.2 mmol) and 2-aminothiazol (0.357 g, 3.2 mmol) were dissolved in 25 ml DMF and cooled to 0° C. Triethylamine (1.1 ml, 7.6 mmol) was added, followed by DEPC (0.613 ml, 3.7 mmol). After stirring at 0° C. for 2 h and at room temperature for 24 h the reaction mixture was diluted with ethyl acetate/toluene (2:1), washed with 1M aqueous potassium hydrogen sulfate, water, saturated aqueous NaHCO$_3$ and aqueous NaCl, dried over sodium sulfate and concentrated in vacuo. The crude product was purified by crystallization from ethyl acetate/hexane to give a white solid (0.526 g). Rf: 0.26 (ethyl acetate/hexane 1:1)

ESI-MS: 395.2 [M+H]$^+$, calc. C$_{13}$H$_{26}$N$_4$O$_4$S=394.3

Synthesis of prolyl-prolyl-thiazolyl(2)-amide

To a solution of N-(t-butoxycarbonyl)-prolyl-prolylthiazolyl(2)-amide in dichloromethane (2 ml) was added trifluoroacetic acid (2 ml). After stirring for 2 h, the reaction mixture was concentrated in vacuo. Reevaporation of the residue with toluene (5×10 ml) gave the deprotected product which was used in the next step without further purification.

Synthesis of (3R,4S)-4-[N-(N,N-dimethyl-L-valyl-L-valyl)-N-methylamino]-3-methoxy-5-methyl-hexanoyl-prolylprolyl-thiazolyl(2)-amide (compound 1)

To a precooled solution of 0.1 g (3R,4S)-4-[N-(N,N-dimethyl-L-valyl-L-valyl)-N-methylamino]-3-methoxy-5-methylhexanoic acid (0.20 mmol) and 0.08 g prolyl-prolyl-thiazolyl(2)-amide (0.20 mmol) in 1 ml DMF were added 0.037 ml DEPC (0.22 mmol) and 0.096 ml triethylamine (0.66 mmol). After stirring at 0° C. for 2 h and at room temperature for 24 h, the reaction mixture was diluted with ethyl acetate/toluene (2:1), washed with 1M aqueous potassium hydrogen sulfate, water, saturated aqueous NaHCO$_3$ and aqueous NaCl, dried over sodium sulfate and concentrated in vacuo. The crude product was purified via preparative HPLC to yield 112 mg of the desired product as a white solid.

ESI-MS: 692 [M+H]$^+$, calc. C$_{34}$H$_{57}$N$_7$O$_6$S=691

Example 2

Synthesis of (3R,4S)-4-[N-(N,N-dimethyl-L-valyl-L-valyl)-N-methylamino]-3-methoxy-5-methyl-hexanoyl-prolyl-prolyl-benzylamide (compound 2; SEQ ID NO:1)

To a precooled solution of 0.15 g (3R,4S)-4-[N-(N,N-dimethyl-L-valyl-L-valyl)-N-methylamino)-3-methoxy-5-methyl-hexanoic acid (0.30 mmol) and 0.15 g prolyl-prolylbenzylamide (0.30 mmol) in 2 ml DMF were added 0.2 ml DEPC (1.2 mmol) and 0.2 ml triethylamine (2.33 mmol). After stirring at 0° C. for 2 h and at room temperature for 24 h, the reaction mixture was diluted with ethyl acetate/toluene (2:1), washed with 1M aqueous potassium hydrogen sulfate, water, saturated aqueous NaHCO$_3$ and aqueous NaCl, dried over sodium sulfate and concentrated in vacuo. The crude product was purified via preparative HPLC to yield 161 mg of the desired product as a white solid.

ESI-MS: 699 [M+H]$^+$, calc. C$_{38}$H$_{62}$N$_6$O$_6$=698

Example 3

Synthesis of (3R,4S,5S)-4-[N-(N,N-dimethyl-L-Valyl-L-valyl)-N-methylamino]-3-methoxy-5-methyl-heptanoyl-prolyl-prolyl-isopropylamide (Compound 3; SEQ ID NO:1)

Synthesis of N-Benzyloxycarbonyl-prolyl-isopropylamide

N-Benzyloxycarbonyl-proline (25 g, 0.1 mol) was dissolved in 450 ml dichloromethane. Then, 11.07 ml isopropylamine (0.13 mol) was added, followed by 7.66 g HOBt (0.05 mol), 24.92 g EDCI (0.13 mol) and 60.85 ml diisopropylethylamine (0.35 mol). The reaction mixture was stirred at room temperature overnight, further diluted with dichloromethane and washed with 5% citric acid (2×), saturated sodium hydrogen carbonate (1×), and water (1×). The organic layer was dried over sodium sulfate and concentrated in vacuo to yield 28.48 g of the product as an off-white solid.

MS (EI): $M^+=290$.

Synthesis of Prolyl-isopropylamide

N-Benzyloxycarbonyl-prolyl-isopropylamide (28.48 g, 98.2 mmol) was dissolved in 75 ml methanol. This solution was added to a slurry of 3 spatulafuls of 10% Pd/C in 50 ml methanol under a stream of nitrogen. The reaction mixture was hydrogenated for 4 h, filtered over celite, washed with methanol, and the solvent evaporated under reduced pressure to give 16 g of a yellow crystalline solid. This material was dissolved in dichloromethane and washed with 5% citric acid (2×). The combined acidic aqueous layers were brought to pH 12 with 1N NaOH and solid NaOH, and extracted with dichloromethane (2×). The combined organic extracts were dried over sodium sulfate and concentrated in vacuo to yield 14.2 g of an off-white crystalline solid.

MS (CI): $M^+=157$.

Synthesis of (3R,4S,5S)-4-[N-(N,N-dimethyl-L-valyl-L-valyl)-Nmethylamino)-3-methoxy-5-methyl-heptanoyl-prolyl-prolyl-isopropylamide (compound 3)

(3R,4S,5S)-4-[N-(N,N-dimethyl-L-valyl-L-valyl)-N-methylamino)-3-methoxy-5-methyl-heptanoyl-proline (0.45 g, 0.855 mmol) and 0.147 g prolyl-isopropylamide (0.940 mmol) were dissolved in 15 ml dichloromethane. After addition of 0.065 g HOBt (0.428 mmol), 0.18 g EDCI (0.94 mmol) and 0.44 g ml diisopropylethylamine. The reaction mixture was stirred at room temperature overnight. Additional reagents were added (0.073 g prolyl-isopropylamide, 0.032 g HOBt, 0.09 g EDCI, 0.223 ml diisopropylethylamine) and stirring continued at room temperature overnight. The reaction mixture was concentrated in vacuo, redissolved in ethyl acetate, and washed with saturated aqueous $NaHCO_3$, brine, and 5% citric acid. The acidic aqueous layers were brought to pH 10 with 1N NaOH and extracted with ethyl acetate (2×). The combined organic extracts were concentrated in vacuo. The residue was dissolved in 100 ml water and lyophilized to give 330 mg of the product as a fluffy white solid.

ESI-MS: 665.5 $[M+H]^+$

The following compounds can be prepared according to the methods described in Examples 1,2, and 3:

| COMPOUND | COMPOUND SEQUENCE |
| --- | --- |
| 4 | Xaa Val Xae Pro Xaf |
| 5 | Xaa Val Xae Pro Xag |
| 6 | Xaa Val Xae Pro Xah |
| 7 | Xaa Val Xae Pro Xaz |
| 8 | Xaa Val Xae Pro Xby |
| 9 | Xaa Val Xad Pro Xby |
| 10 | Xaa Val Xae Pro Xai |
| 11 | Xaa Val Xae Pro Xak |
| 12 | Xaa Val Xae Pro Xal |
| 13 | Xaa Val Xae Pro Xam |
| 14 | Xaa Val Xae Pro Xan |
| 15 | Xaa Val Xae Pro Xao |
| 16 | Xaa Val Xae Pro Xap |
| 17 | Xaa Val Xae Pro Xaq |
| 18 | Xaa Val Xae Pro Xar |
| 19 | Xaa Val Xae Pro Xas |
| 20 | Xaa Val Xae Pro Xat |
| 21 | Xaa Val Xae Pro Xau |
| 22 | Xaa Val Xae Pro Xav |
| 23 | Xaa Val Xae Pro Xaw |
| 24 | Xaa Val Xae Pro Xax |
| 25 | Xaa Val Xae Pro Xay |
| 26 | Xaa Val Xae Pro Xba |
| 27 | Xaa Val Xae Pro Xbb |
| 28 | Xaa Val Xae Pro Xbc |
| 29 | Xaa Val Xae Pro Xbd |
| 30 | Xaa Val Xae Pro Xbe |
| 31 | Xaa Val Xae Pro Xbf |
| 32 | Xaa Val Xae Pro Xbg |
| 33 | Xaa Val Xae Pro Xbh |
| 34 | Xaa Val Xae Pro Xbi |
| 35 | Xaa Val Xae Pro Xbk |
| 36 | Xaa Val Xae Pro Xbl |
| 37 | Xaa Val Xae Pro Xbm |
| 38 | Xaa Val Xae Pro Xbn |
| 39 | Xaa Val Xae Pro Xbp |
| 40 | Xaa Val Xae Pro Xbq |
| 41 | Xaa Val Xae Pro Xbr |
| 42 | Xaa Val Xae Pro Xbs |
| 43 | Xaa Val Xae Pro Xbt |
| 44 | Xaa Val Xae Pro Xbv |
| 45 | Xaa Val Xae Pro Xbw |
| 46 | Xaa Val Xae Pro Xbx |
| 47 | Xaa Val Xad Pro Xaf |
| 48 | Xaa Val Xad Pro Xag |
| 49 | Xaa Val Xad Pro Xah |
| 50 | Xaa Ile Xad Pro Xaf |
| 51 | Xaa Ile Xad Pro Xag |
| 52 | Xaa Ile Xad Pro Xah |
| 53 | Xaa Val Xad Pro Xai |
| 54 | Xaa Val Xad Pro Xak |
| 55 | Xaa Val Xad Pro Xal |
| 56 | Xaa Val Xad Pro Xam |
| 57 | Xaa Val Xad Pro Xan |
| 58 | Xaa Val Xad Pro Xao |
| 59 | Xaa Val Xad Pro Xap |
| 60 | Xaa Val Xad Pro Xaq |
| 61 | Xaa Val Xad Pro Xar |
| 62 | Xaa Val Xad Pro Xas |
| 63 | Xaa Val Xad Pro Xat |
| 64 | Xaa Val Xad Pro Xau |
| 65 | Xaa Val Xad Pro Xav |
| 66 | Xaa Val Xad Pro Xaw |
| 67 | Xaa Val Xad Pro Xax |
| 68 | Xaa Val Xad Pro Xay |
| 69 | Xaa Val Xad Pro Xba |
| 70 | Xaa Val Xad Pro Xbb |
| 71 | Xaa Val Xad Pro Xbc |
| 72 | Xaa Val Xad Pro Xbd |
| 73 | Xaa Val Xad Pro Xbe |
| 74 | Xaa Val Xad Pro Xbf |
| 75 | Xaa Val Xad Pro Xbg |
| 76 | Xaa Val Xad Pro Xbh |
| 77 | Xaa Val Xad Pro Xbi |
| 78 | Xaa Val Xad Pro Xbk |
| 79 | Xaa Val Xad Pro Xbl |
| 80 | Xaa Val Xad Pro Xbm |
| 81 | Xaa Val Xad Pro Xbn |
| 82 | Xaa Val Xad Pro Xbo |
| 83 | Xaa Val Xad Pro Xbp |
| 84 | Xaa Val Xad Pro Xbq |
| 85 | Xaa Val Xad Pro Xbr |
| 86 | Xaa Val Xad Pro Xbs |
| 87 | Xaa Val Xad Pro Xbt |
| 88 | Xaa Val Xad Pro Xbv |
| 89 | Xaa Val Xad Pro Xbw |
| 90 | Xaa Val Xad Pro Xbx |
| 91 | Xab Val Xae Pro Xbo |

-continued

| COMPOUND | COMPOUND SEQUENCE |
|---|---|
| 92 | Xac Val Xae Pro Xbo |
| 93 | Xaa Ile Xae Pro Xbo |
| 94 | Xaa Xbu Xae Pro Xbo |
| 95 | Xab Val Xad Pro Xbo |
| 96 | Xac Val Xad Pro Xbo |
| 97 | Xaa Ile Xad Pro Xbo |
| 98 | Xaa Xbu Xad Pro Xbo |
| 99 | Xaa Val Xae Pro Xbz |

The symbols X in the summary have the following meanings:

Xaa: N,N-Dimethyl-valine
Xab: N,N-Dimethylisoleucine
Xac: N,N-Dimethyl-tert-leucine Xad: 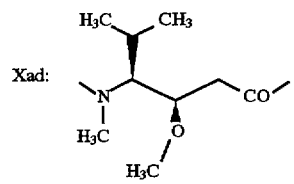

Xae: 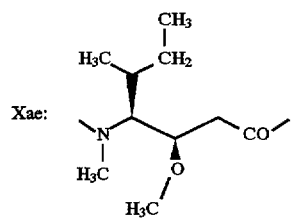

Xaf: 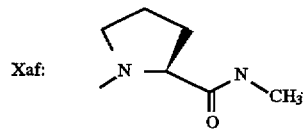

Xag: 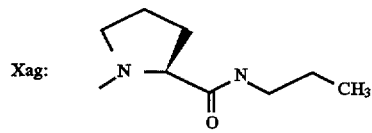

Xah: 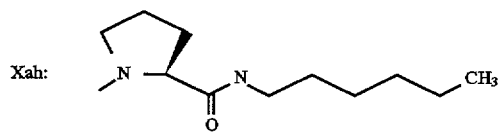

Xai: 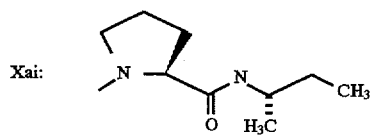

Xak: 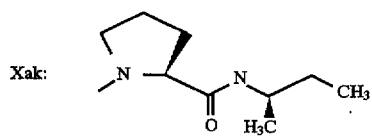

Xal: 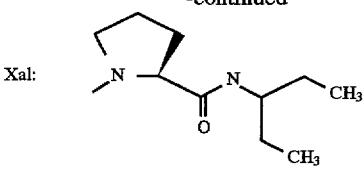

Xam: 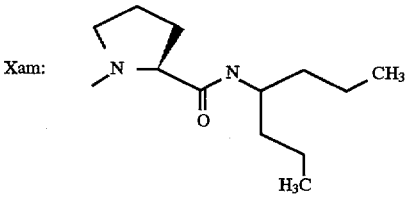

Xan: 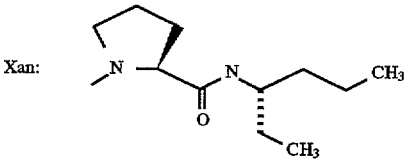

Xao: 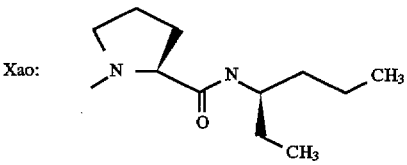

Xap: 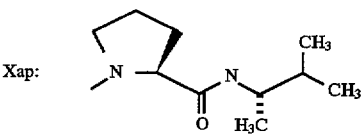

Xaq: 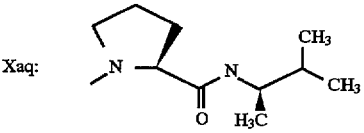

Xar: 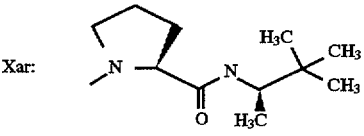

Xas: 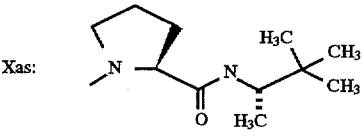

Xat: 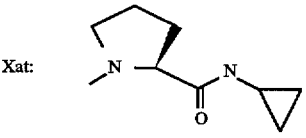

Xau: 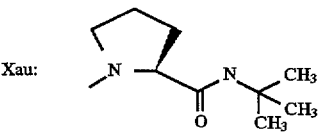

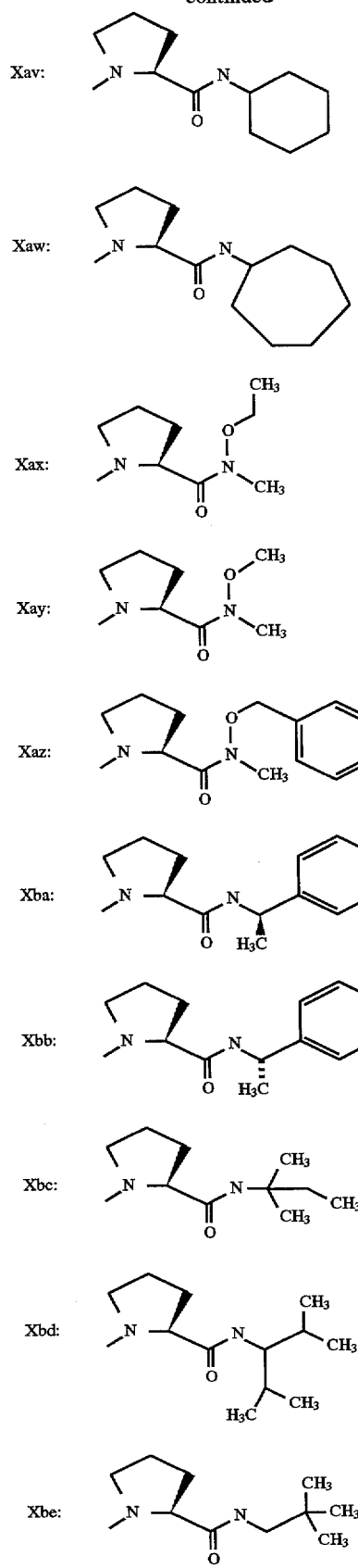
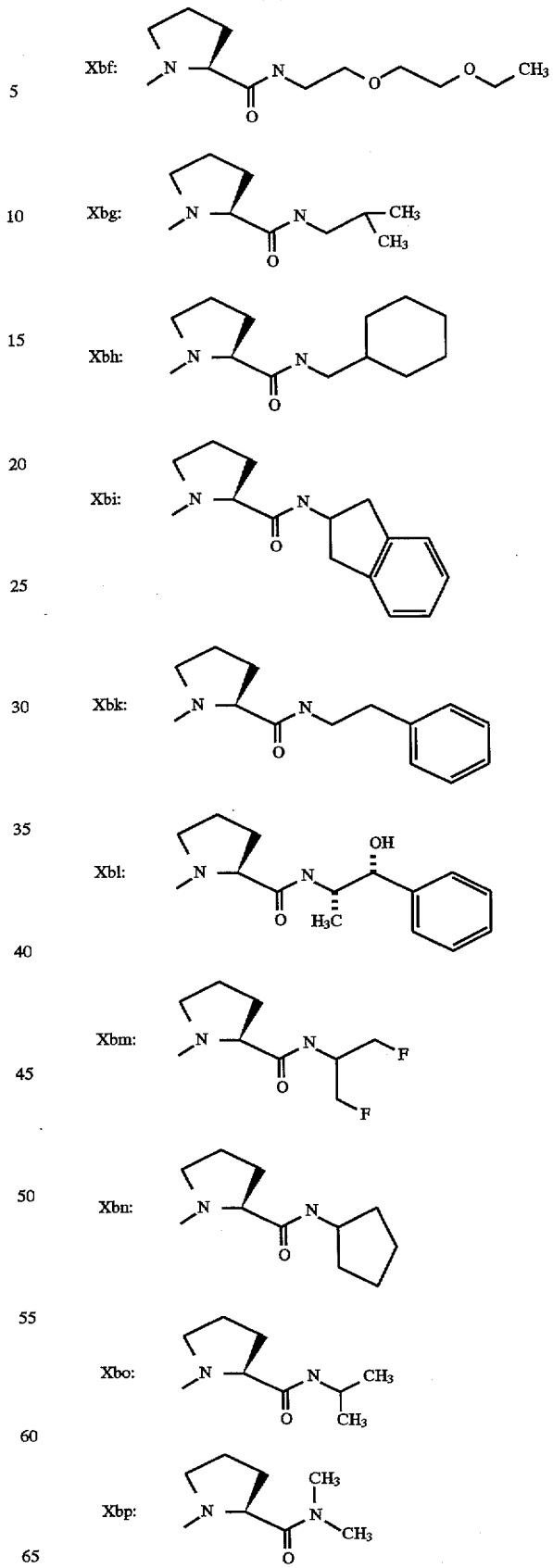

-continued

Xbq: 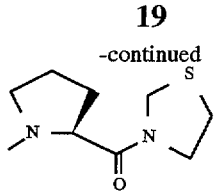

Xbr: 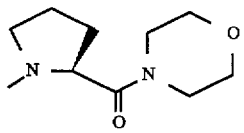

Xbs: 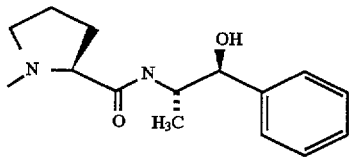

Xbt: 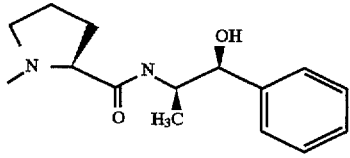

Xbu:   2-tert.butylglycine

Xbv: 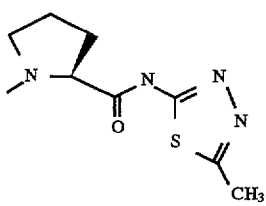

Xbw: 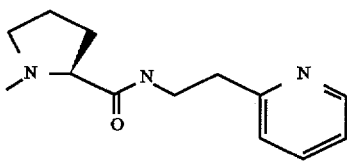

Xbx: 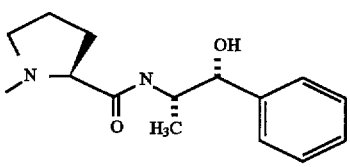

Xby:   prolyl tert.butylester

Xbz   prolyl benzylamide

The sequence corresponding to compounds 1–99 are listed below:

| Compounds | |
|---|---|
| 1–49; 53–92, 99 | SEQ ID NO: 1 |
| 50–52, 93, 97 | SEQ ID NO: 2 |
| 94, 98 | SEQ ID NO: 3 |
| 95 | SEQ ID NO: 4 |
| 96 | SEQ ID NO: 5 |

Example 4

Determination of In Vitro Cytotoxicity

Cytotoxicity was measured using the microculture tetrazolium assay (MTT), a standard methodology for adherent cell lines. Details of this assay have been published (Alley, et al., *Cancer Research* 48: 589–601 (1988)). Exponentially growing cultures of HT-29 colon carcinoma cells were used to make microtiter plate cultures. Cells were seeded at 5000–20,000 cells per well in 96-well plates (in 150 μl of media), and grown overnight at 37° C. Test compounds were added in 10-fold dilutions varying from $10^{-4}$M to $10^{-10}$M. Cells were then incubated for 48 hours. To determine the number of viable cells in each well, the MTT dye was added (50 μl of 3 mg/ml solution of 3-(4,5-dimethylthiazol-2-yl)-2,5-diphenyltetrazolium bromide in saline). This mixture was incubated at 37° C. for 5 hours, and then 50 μl of 25% SDS, pH 2, was added to each well. After an overnight incubation, the absorbance of each well at 550 nm was read using an ELISA reader. The values for the mean±SD of data from replicated wells were calculated, using the formula % T/C (% viable cells treated/control).

$$\frac{OD \text{ of treated cells}}{OD \text{ of control cells}} \times 100 = \% \ T/C$$

The concentration of test compound which gives a T/C of 50% growth inhibition was designated as the $IC_{50}$ value.

Results

The results of the in vitro evaluation are shown in the table below. The IC50 values shown are in the nanomolar range, indicating that these compounds possess significant activity in the HT-29 system.

TABLE

| COMPOUND | $IC_{50}$ (M) |
|---|---|
| 1 | $2 \times 10^{-9}$ |
| 2 | $4 \times 10^{-9}$ |
| 3 | $6 \times 10^{-9}$ |

Example 5

Determination of In Vivo Activity

Compounds of this invention can be tested in a pre-clinical assay for in vivo activity which is indicative of clinical utility. Such assays are typically conducted with nude mice into which tumor tissue, preferably of human origin, had been transplanted (xenografted), as is well known in this field. Test compounds are evaluated for anti-tumor efficacy following administration to the xenograft-bearing mice.

For example, human breast tumors (MX-1) which have been grown in athymic nude mice are transplanted into new recipient mice, using tumor fragments of about 50 mg in size. The day of transplantation is designated as day 0. The mice are divided into four groups of 5–10 mice each. An untreated group serves as the control. Doses can be, for example, administered on a schedule such as on days 5, 7, 9, 12, 14, 16, 19, 21 and 23 post-implantation.

Tumor diameters and body weights are measured twice weekly. Tumor volumes are calculated using the diameters measured with Vernier calipers, and the formula (length×width$^2$)/2=mm$^3$ of tumor volume Mean tumor volumes are calculated for each treatment group, and T/C values determined for each group relative to the untreated control tumors.

In another in vivo assay, the P388 murine lymphocytic leukemia is harvested from donor mice by peritoneal lavage at day 7 post-transplant and administered to test mice. Treatment of test mice begins 3 days post-transplant and the drugs are administered for five consecutive days. The survival time for untreated mice is typically between 11 and 13 days. The data are expressed as mean survival time (MST) and tretade/control %. According to National Cancer Institute guidelines, a T/C in the range of 128–190% indicates a drug with moderate to good activity.

Equivalents

Those skilled in the art will recognize or be able to ascertain using no more than routine experimentation many equivalents to the specific embodiments of the invention described herein. Such equivalents are intended to be encompassed in the scope of the following claims.

(y = 0, 1, 2, 3, 4, or 5), $-NH-(CH_2CH_2O)_y-CH_3$ (y = 0, 1, 2, 3, 4, or 5), $-NH-NH-C_6H_5$, $-NH-N(CH_3)C_6H_5$, $-NH-NH-CH_2-C_6H_5$, $-NH-N(CH_3)CH_2-C_6H_5$,

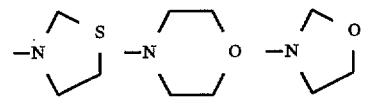

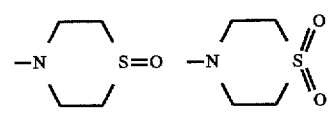

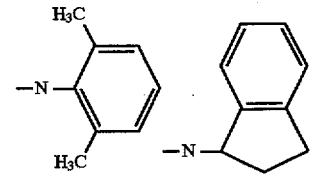

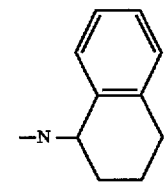

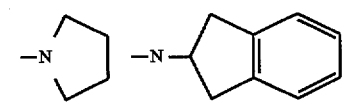

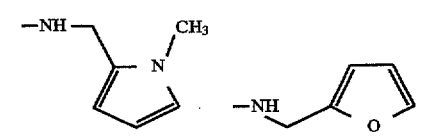

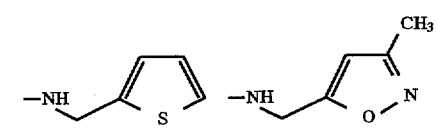

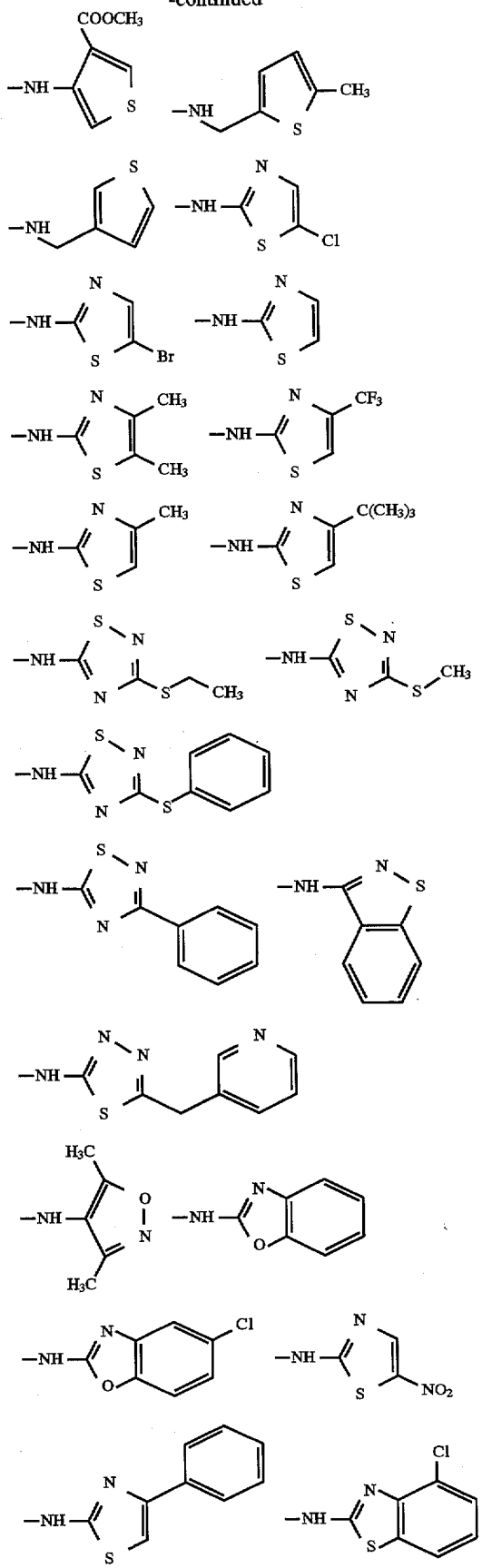
-continued

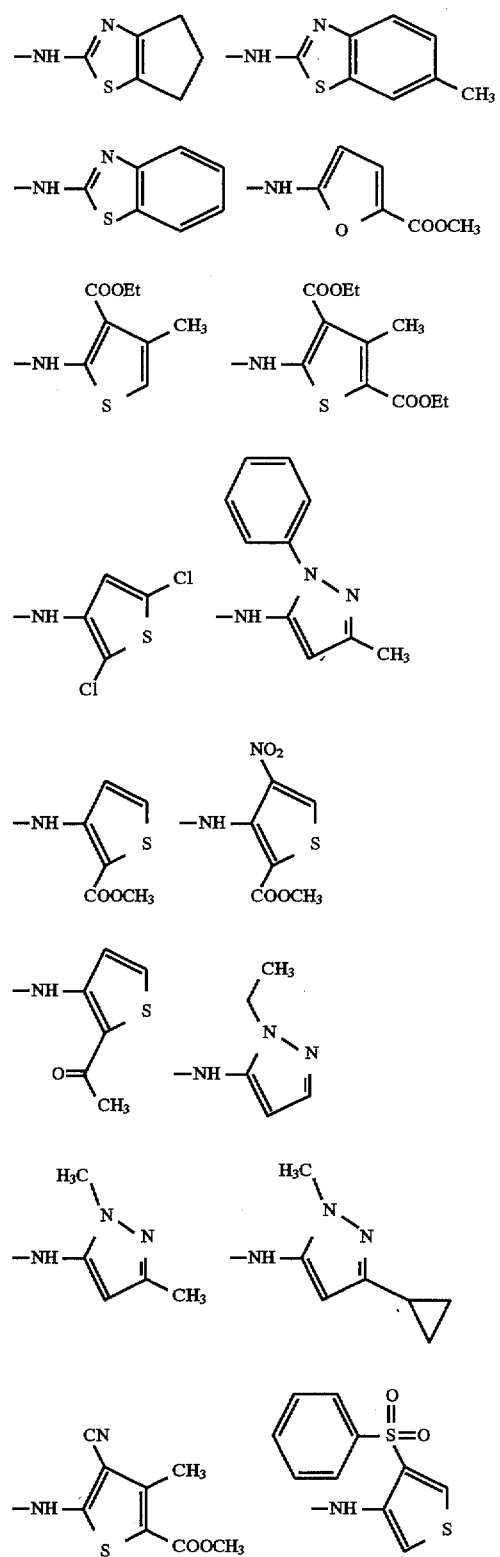
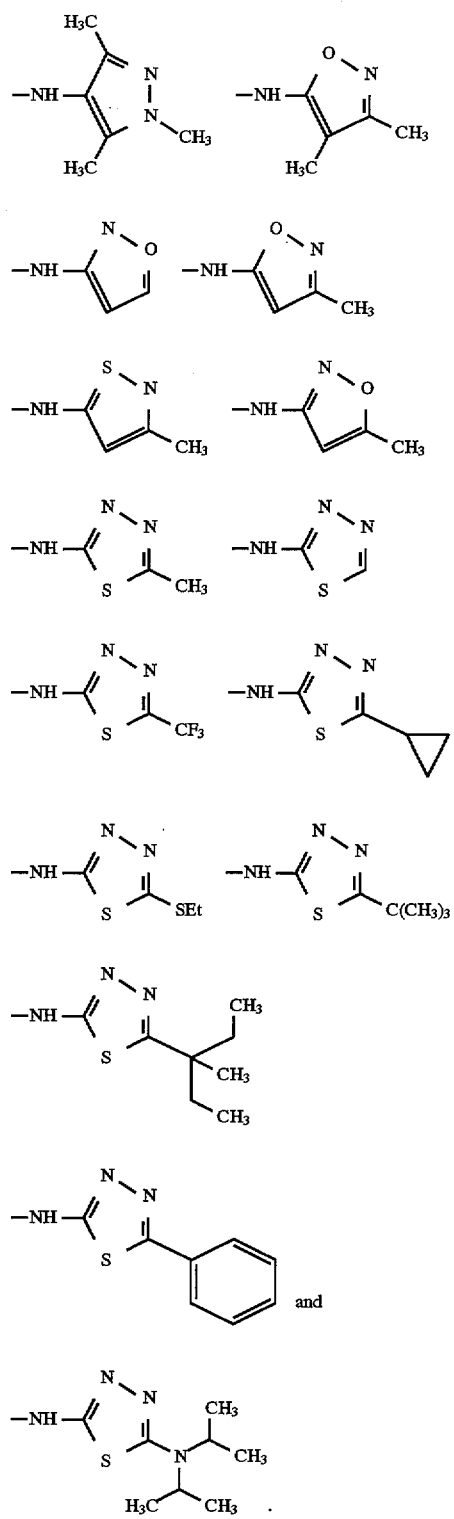

We claim:

1. A compound of Formula I,

A-B-N(CH₃)-CHD-CH(OCH₃)-CH₂CO-Pro-Pro-K    (I), wherein A is an amino acid residue of the formula (CH₃)₂N—CHX—CO, wherein X is a normal or branched C₃-C₄-alkyl group; B is an amino acid residue selected from the group consisting of valyl, isoleucyl, leucyl, and 2-'butylglycyl; D is a normal or branched C₂-C₅-alkyl group; and K is a t-butoxy group or a substituted amino group; or a salt thereof with a pharmaceutically acceptable acid.

2. The compound of claim 1 wherein K is a substituted amino group selected from the group consisting of —N(C₁₋₃-alkyl)C₁₋₃-alkyl, normal or branched —NH—C₁₋₈-alkyl, —NH—C(CH₃)₂CN, —NH—C(CH₃)₂CCH, —NH—C(CH₃)₂CH₂CH₂OH, —NH—C(CH₃)₂CH₂OH, —NH—C₃₋₈-cycloalkyl, —NH—[3,3,0]-bicyclooctyl, —NHCH(CH₃)C(OH)C₆H₅, —NH-quinolyl, —NH-pyrazyl, —NH—CH₂-benzimidazolyl, —NH-adamantyl, —NH—CH₂-adamantyl, —NH—CH(CH₃)-phenyl, —NH—C(CH₃)₂-phenyl, —N(C₁₋₄-alkoxy)-C₁₋₄-alkyl, —N(C₁₋₄-alkoxy)-CH₂-phenyl, —N(C₁₋₄-alkoxy)phenyl, —N(CH₃)O-phenyl, —NH—(CH₂)ᵥ-phenyl (v=0,1,2, or 3), —NH—(CH₂)ₘ-naphthyl (m=0 or 1), —NH—(CH₂)ᵥᵥ-benzhydryl (w=0,1, or 2), —NH-biphenyl, —NH-pyridyl, —NH—CH₂-pyridyl, —NH—CH₂—CH₂-pyridyl, —NH-benzothiazolyl, —NH-benzoisothiazolyl, —NH-benzopyrazolyl, —NH-benzoxazolyl, —NH—(CH₂)ₘ-fluorenyl (m=0 or 1), —NH-pyrimidyl, —NH—(CH₂)ₘ-indanyl (m=0 or 1), —NH—(CH₂CH₂O)ᵧ—CH₂CH₃.

3. The compound of claim 1 wherein X is an isopropyl, t-butyl or sec-butyl group; B is valyl, isoleucyl, or 2-t-butylglycyl; D is an isopropyl, t-butyl or sec-butyl group; and K is a t-butoxy group or a substituted amino group.

4. The compound of claim 3 wherein K is a substituted amino group selected from the group consisting of —NHCH₃, —NHCH₂CH₃, —NH(CH₂)₂CH₃, —NH(CH₂)₃CH₃, —NH(CH₂)₄CH₃, —NH(CH₂)₅CH₃, —NHCH(CH₃)₂, —NHCH(CH₂CH₃)₂, —NHCH(CH₂CH₂CH₂)₂, —NHC(CH₃)₃, —NHCH[CH(CH₃)₂]₂, —NHCH(CH₂CH₃)CH₂CH₂CH₃, —NHCH(CH₃)CH₂CH₃, —NHCH₂CH₂F, —NHC(CH₃)₂CH₂CH₃, —NHCH(CH₃)CH(CH₃)₂, —NHCH(CH₃)C(CH₃)₃, —NHCH(CH₃)CH₂CH₂CH₃, —NHCH₂CH(CH₃)₂, —NHCH₂C(CH₃)₃, —NH-cyclopropyl, —NH-cyclobutyl, —NH-cyclopentyl, —NH-cyclohexyl, —NH-cycloheptyl, —N(CH₃)OCH₃, —N(CH₃)₂, —N(CH₃)OCH₂CH₃, —N(CH₃)OCH₂CH₂CH₃, —N(CH₃)OCH(CH₃)₂, —N(CH₂CH₃)OCH₃, —N(CH₂CH₃)OCH₂CH₃, —N(CH₃)OCH₂C₆H₅, —N(OCH₃)CH₂—C₆H₅, —N(CH₃)OC₆H₅, —NH—CH₂—C₆H₅, —NH(CH₂)₂C₆H₅, —NH(CH₂)₃C₆H₅, —NHCH(CH₃)CH(OH)C₆H₅, —NH—CH₂-cyclohexyl, —NH-indanyl-(1), —NH—CH₂CF₃, —NHCH(CH₂F)₂, —NHC(CH₃)₂CH₂OH, —NH(CH₂CH₂O)₂CH₂CH₃, —NHC(CH₃)₂CN, —NH-quinolyl, —NH-pyrazyl, —NH-adamantyl(2), —NH-adamantyl(1), —NH—CH₂-naphthyl, —NH-benzhydryl, —NH-biphenyl, —NH-pyridyl, —NH—CH₂-pyridyl, —NH—CH₂-CH₂-pyridyl, —NH-benzothiazolyl, —NH-benzoisothiazolyl, —NH-benzopyrazolyl, —NH-benzoxazolyl, —NH-fluorenyl, —NH-pyrimidyl, —NH—CH₂-(4-methyl)thiazolyl(2), —NH—CH₂-furanyl(2), —NH—CH₂-thienyl(2), —NH—CH₂-(5-methyl)thienyl(2), —NH-thiazolyl(2), —NH-isoxazolyl(3), —NH-(3-methyl)isoxazolyl(5), —NH-(3-methyl)isothiazolyl(5), —NH-(5-trifluoromethyl)thiadiazolyl(2), —NH-(5-cyclopropyl)thiadiazolyl(2), —NH-(4,5-dimethyl)thiadiazolyl(2), —NH-(5-methyl)thiadiazolyl(2),

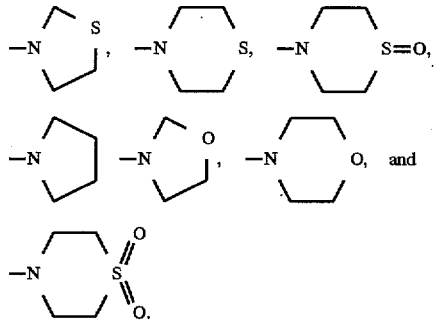

5. The compound of claim 3 wherein K is a substituted amine selected from the group consisting of —NHCH₃, —N(CH₃)₂, —NH(CH₂)₂CH₃, —NHCH(CH₃)₂, —NHCH[CH(CH₃)₂]₂, —NHCH(CH₃)CH₂CH₃, —NH(CH₂)₅CH₃, —NHCH(CH₂CH₃)₂, —NHCH(CH₃)₂CH₂CH₃, —NHCH(CH₂CH₂CH₃)₂, —NHC(CH₃)₃, —NHCH(CH₂CH₃)CH₂CH₂CH₃, —NHCH(CH₃)C(CH₃)₃, —NHCH₂CH(CH₃)₂, —NHCH₂C(CH₃)₃, —NH-cyclopropyl, —NH-cyclopentyl, —NH-cyclohexyl, —NH-cycloheptyl, —N(CH₃)OCH₃, —N(CH₃)(OCH₂CH₃), —N(CH₃)OCH₂C₆H₅, —NH—CH(CH₃)—C₆H₅, —NHCH₂CH₂C₆H₅, —NHCH(CH₃)CH(OH)C₆H₅, —NH—CH₂-cyclohexyl, —NH—(CH₂CH₂O)₂CH₂CH₃, —NH-indanyl-(1), —NHCH(CH₂F)₂, —NHC(CH₃)₂CN, —NH—CH₂—CH₂-pyridyl, 4-morpholinyl, 2-thiazolidinyl, and —NH-(5-methyl)thiadiazolyl(2).

6. The compound of claim 5 wherein X is isopropyl, B is valyl, and D is isopropyl or sec-butyl.

7. A pharmaceutical composition comprising a pharmaceutically acceptable carrier and a therapeutically effective amount of a compound of claim 1.

8. A method for treating a tumor in a mammal, comprising administering to the mammal a tumor-inhibiting amount of a compound of claim 1, wherein the tumor is a colon tumor, a breast tumor or a lung tumor.

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Val Val Xaa Pro Pro
    1                   5

( 2 ) INFORMATION FOR SEQ ID NO:2:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Val Ile Xaa Pro Pro
    1                   5

( 2 ) INFORMATION FOR SEQ ID NO:3:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:3:

Val Xaa Xaa Pro Pro
    1                   5

( 2 ) INFORMATION FOR SEQ ID NO:4:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:4:

Ile Val Xaa Pro Pro
    1                   5

( 2 ) INFORMATION FOR SEQ ID NO:5:

( i ) SEQUENCE CHARACTERISTICS:
        ( A ) LENGTH: 5 amino acids
        ( B ) TYPE: amino acid
        ( C ) STRANDEDNESS: single
        ( D ) TOPOLOGY: linear (ii) MOLECULE TYPE: peptide (xi) SEQUENCE DESCRIPTION: SEQ ID NO:5:

Xaa Val Xaa Pro Pro
1               5